United States Patent [19]
Charlton et al.

[11] Patent Number: 5,854,074
[45] Date of Patent: *Dec. 29, 1998

[54] DISPENSING INSTRUMENT FOR FLUID MONITORING SENSORS

[75] Inventors: Steven C. Charlton, Osceola, Ind.; Anne T. Miller, Cambridge, United Kingdom; Joseph L. Moulton, Mishawaka, Ind.; Matthew A. Schumann, Cambridge, United Kingdom; Dennis Slomski, South Bend; Frank W. Wogoman, Granger, both of Ind.

[73] Assignee: Bayer Corporation, Elkhart, Ind.

[*] Notice: This patent issued on a continued prosecution application filed under 37 CFR 1.53(d), and is subject to the twenty year patent term provisions of 35 U.S.C. 154(a)(2).

[21] Appl. No.: 785,185

[22] Filed: Jan. 17, 1997

Related U.S. Application Data

[62] Division of Ser. No. 404,303, Mar. 14, 1995, Pat. No. 5,630,986.

[51] Int. Cl.⁶ .................................................. G01N 37/00
[52] U.S. Cl. ............................... 436/46; 436/43; 436/44; 422/61; 422/63; 422/104; 221/87; 221/88; 221/268
[58] Field of Search .................................. 422/55, 58, 63, 422/64, 65, 66, 99, 104; 436/43, 44, 46, 164, 805, 810; 435/805, 808; 221/31, 87, 88, 268; 206/828

[56] References Cited

U.S. PATENT DOCUMENTS 5,489,414  2/1996  Schreiber et al. ........................ 422/64
5,575,403  11/1996  Charlton et al. ........................ 221/31

Primary Examiner—Long V. Le
Attorney, Agent, or Firm—Jerome L. Jeffers

[57] ABSTRACT

A sensor dispensing instrument is adapted to receive a generally circular sensor pack containing a plurality of blood glucose sensors. Each of the sensors are disposed in sensor cavities, each of which is in fluid communication with a corresponding desiccant cavity and has a support wall that assists in directing the sensor as its being ejected from the cavity. The sensor pack is loaded on an indexing disk in the instrument such that when a slide actuator on the instrument is moved toward a testing position, a feed mechanism engaged by the slide actuator moves a knife blade thereon toward one of the sensor cavities. The knife blade pierces a portion of a foil covering the sensor cavity and engages the sensor disposed in the cavity to thereby eject the sensor from the sensor cavity. The continued sliding of the slide actuator toward its testing position results in the sensor being completely ejected from the sensor cavity and disposed in a testing position with a testing end of the sensor projecting from the instrument. Once the blood analyzing test is completed, the slide actuator is moved in the opposite direction towards its standby position. As the slide actuator is moved away from its testing position, the indexing disk with the sensor pack thereon is rotated so that the next one of sensor cavities is positioned so that the sensor therein can be used for the next blood glucose test that is to be performed. The instrument includes circuitry to obtain test data from the sensor pack and to display testing data.

2 Claims, 7 Drawing Sheets

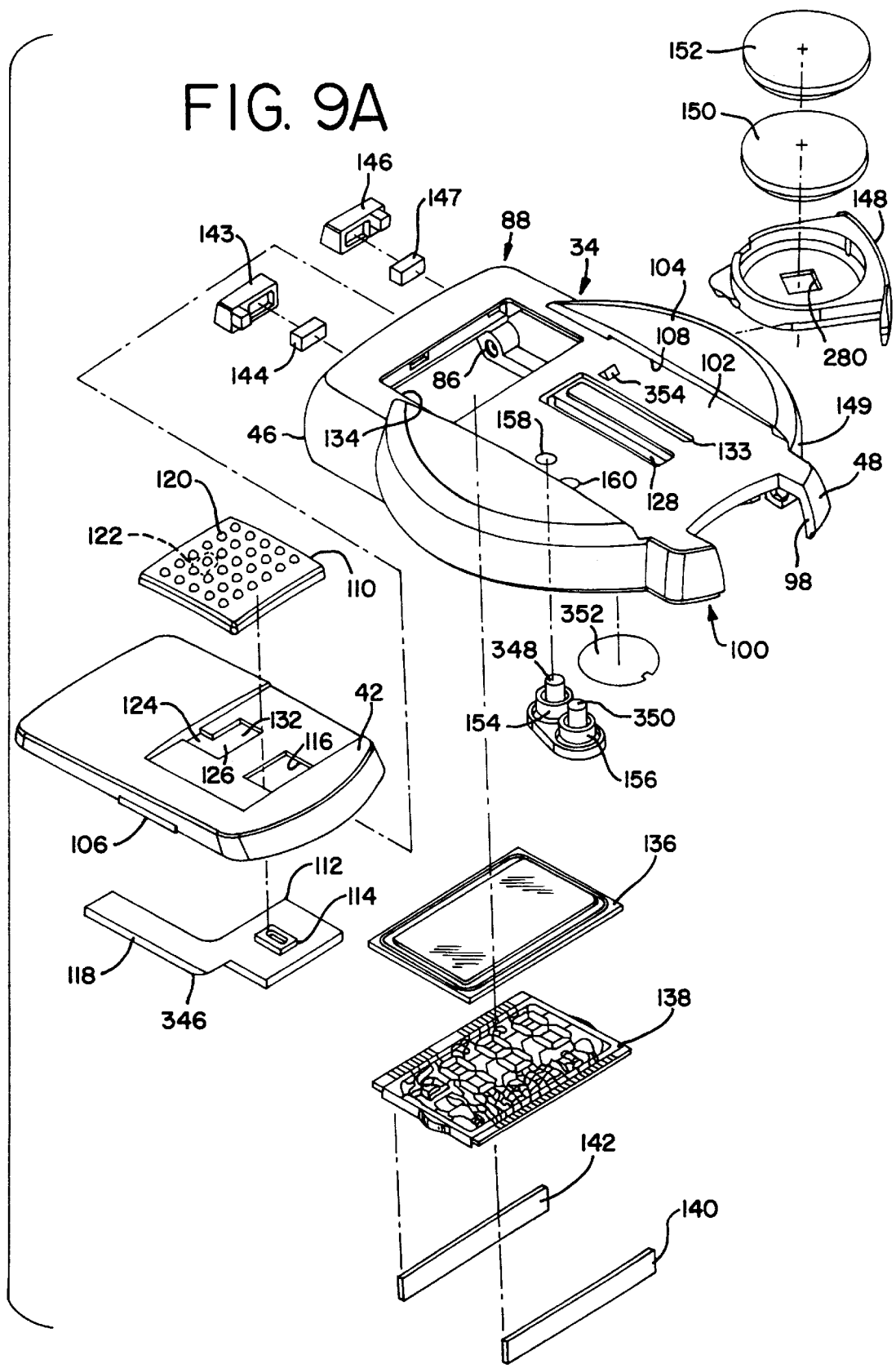

DISPENSING INSTRUMENT FOR FLUID MONITORING SENSORS

This is a divisional application of application Ser. No. 08/404,303, filed on Mar. 14, 1995, now U.S. Pat. No. 5,630,986.

BACKGROUND OF THE INVENTION

1. Field of the Invention

The present invention generally relates to a fluid monitoring system, and, more particularly, to a new and improved instrument for handling multiple sensors that are used in analyzing blood glucose or other analytes contained therein.

2. Description of the Prior Art

People suffering from various forms of diabetes routinely need to test their blood to determine the level of blood glucose. The results of such tests can be used to determine what, if any, insulin or other medication needs to be administered. In one type of blood glucose testing system, sensors are used to test a sample of blood.

Such a sensor may have a generally flat, rectangular shape with a front or testing end and a rear or contact end. The sensor contains biosensing or reagent material that will react with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor with the result that an electrical signal indicative of the blood glucose level in the blood being tested is supplied to contact areas located near the rear or contact end of the sensor.

In order to couple the electrical signals produced at the sensor contacts to monitoring equipment, the sensors need to be inserted into sensor holders prior to the sensor end being placed into the fluid being tested. The holders have corresponding mating contact areas that become coupled to the contacts on the sensor when the sensor is inserted into the holder. Consequently, the holders act as an interface between the sensor and monitoring equipment that accumulates and/or analyzes the test results.

Prior to being used, the sensors need to be maintained at an appropriate humidity level so as to insure the integrity of the reagent materials in the sensor. Sensors can be packaged individually in tearaway packages so that they can be maintained at the proper humidity level. For instance, blister type packaging methods could be used. In this connection, the packages can include desiccant material to maintain the proper humidity or desiccate level in the package. In order for a person to use an individual sensor for testing blood glucose, the package must be opened by tearing the seal. Alternatively, some packages require the user to exert force against one side of the package resulting in the sensor bursting or rupturing the foil on the other side. As can be appreciated, the opening of these packages can be difficult. Moreover, once the package is opened, the user needs to be sure that the sensor is not damaged or contaminated as it is being placed into the sensor holder and used to test the blood sample.

SUMMARY OF THE INVENTION

Accordingly, an object of the present invention is to provide a new and improved sensor pack of multiple sensors used in testing blood glucose and a dispensing instrument for handling the sensors contained in such sensor packs. In particular, objects of the present invention are to provide a new and improved fluid sensor dispensing instrument handling device that is adapted to receive a sensor pack containing a plurality of fluid sensors so that individual sensors can be selectively placed in a testing position when a feed actuator on the sensor dispensing instrument is moved to a testing position and to automatically index the sensor pack while the feed actuator is being returned to its standby position so that another one of the sensors can be placed into a testing position; to provide a new and improved fluid sensor dispensing instrument having a cutting device pivotally mounted on a driver device with the cutting device ejecting sensors from a sensor pack so as to position the ejected sensor in a testing position and being displaced from the sensor pack as the driver device is returned to a standby position; to provide a new and improved fluid sensor dispensing instrument having a sensor pack with a plurality of cavities for individual sensors with each of the cavities having a support surface for facilitating the ejection of the sensor from the sensor cavity; to provide a new and improved fluid sensor dispensing instrument that provides a contact device to couple individual sensors to data processing equipment in the sensor dispensing instrument so that data from the individual sensors can be displayed; to provide a new and improved fluid sensor dispensing instrument having a calibration mechanism disposed in one hinged portion of the dispensing instrument that is interconnected to data processing equipment in another hinged portion of the dispensing instrument by a somewhat flexible connector disposed in a serpentine configured channel; and to provide a new and improved fluid sensor dispensing instrument having holding devices that intermate with notches on a sensor pack to properly position the sensor pack with respect to an indexing device and to insure that the sensor pack rotates with the indexing device.

In accordance with these and many other objects of the present invention, the present invention is embodied in a sensor dispensing instrument that is adapted to receive a sensor pack containing a plurality of blood glucose sensors. Each of the sensors has a generally flat, rectangular shape with a front testing end through which fluid is drawn so as to react with a reagent material in the sensor and an opposite rear, contact end. The sensor pack includes a generally circular shaped base portion in which is formed sensor retaining cavities or depressions. Each of the sensor retaining cavities is adapted to receive one of the sensors and is in fluid communication with a corresponding desiccant cavity in which is disposed desiccant material. The desiccant material is placed in the cavity to insure that the corresponding sensor cavity is maintained at an appropriate humidity or desiccate level so that the reagent material in the sensors will not be adversely affected prior to the sensors being used. A foil is heat sealed onto the base portion about the entire outer peripheral edge of the base portion and about the entire perimeter of each set of sensor retaining and desciccant cavities to seal the sensor retaining cavities and the desiccant cavities such that the individual sensors are maintained in a desiccated state and isolated from each other. As a result, the opening of one sensor cavity will not affect the desiccated state of any other sensor cavity.

Each of the sensor cavities has a support wall on which the individual sensor lies when the sensor is disposed in the sensor cavity. The support wall extends in a radial direction from adjacent the peripheral edge of the base portion toward a center of the base portion. In order to assist in the ejection of the sensor from the sensor cavity, the support wall includes a sloped or inclined portion that is sloped toward the foil sealing the base portion in a direction toward the peripheral edge of the base portion. The sensor pack additionally includes a series of notches formed along the outer circumferential edge of the sensor pack with each of the notches corresponding to one of the sensor cavities.

The sensor instrument includes an outer housing having an upper case and a lower case with the upper and lower cases being pivotable with respect to each other in a clam shell fashion so that the sensor pack can be positioned in the housing on an indexing disk disposed in the housing. With the sensor pack loaded in the housing, a slide latch on a slide actuator disposed on the upper case of the housing controls whether the movement of the slide actuator places the instrument in a display or data processing mode or in a testing mode.

The instrument is placed into its display mode when the slide latch is moved laterally and the slide actuator is pushed away from its standby position. When in the display mode, a person using the instrument can view data displayed on a display unit in the upper case and/or input data into the instrument.

The instrument is in its testing mode when the slide latch is in its normal position and the slide actuator is pushed towards its testing position. A feeding mechanism engaged by the slide actuator inside the upper case of the housing also is moved from its standby position toward a testing position. The feeding mechanism includes a driver on which is pivotally mounted a knife blade and from which extends an indexing disk drive arm. As the slide actuator is moved towards its actuated position, the driver with the knife blade thereon moves toward the testing position of the feed mechanism and the disk drive arm travels in a straight, radially extending groove in the indexing disk such that the disk is not rotated as the feeding mechanism is moving towards its testing position. The knife blade has cam followers that ride on a first portion of a cam track and under a lift spring as the driver starts to move away from its standby position. The first portion of the track is inclined toward the sensor pack so that the knife blade is moved towards one of the sensor cavities in the sensor pack positioned on the indexing disk. The knife blade pierces the foil covering the sensor cavity in alignment with the knife blade and engages the sensor disposed in the cavity. As the slide actuator and the driver are pushed toward the actuated position of the actuator, the knife blade further severs the foil covering the sensor cavity and forces or ejects the sensor out from the sensor cavity such that a front biased edge of the sensor bursts through the outer foil covering the sensor cavity. As the sensor is being forced out of the sensor cavity, the sensor travels along the sloped support wall of the sensor cavity so that as the sensor is advanced by the knife blade, the sensor will avoid being forced into the heat seal that affixes the foil to the base portion of the sensor pack. The force required to move the sensor through the foil is minimized by the pointed, biased geometry of the front of the sensor so that the sensor cuts an exit hole through the foil rather than merely stretching it.

The continued sliding of the slide actuator toward its testing position results in the sensor being completely ejected from the sensor cavity. A guide disposed near the testing end of the sensor housing guides the sensor from the sensor cavity into a testing position. As this is occurring, cam surfaces on the front of the driver engage a sensor actuator that maintains the sensor in its testing position with the testing end of the sensor projecting out from the testing end of the housing. The sensor actuator includes contacts that become mated with corresponding contacts on the sensor. The sensor dispensing instrument may include a microprocessor or other data processing circuitry that is likewise electrically coupled to the sensor actuator so that data obtained from the sensor when it is inserted into blood to be tested can be processed. The processed data then can be displayed on a screen in the upper case of the instrument or stored for use in other analyzing equipment.

Once the blood analyzing test is completed, the slide actuator is moved in the opposite direction towards its standby position. As the slide actuator is moved away from its testing position, the driver moves away from the sensor actuator so that the contacts on the sensor actuator move away from the corresponding contacts on the sensor and the sensor can be removed from the dispensing instrument. The continued retraction of the driver results in the cam followers on the knife assembly to ride onto the lift spring so that the knife blade is moved away from the sensor pack allowing the indexing disk to advance the sensor pack. In this regard, the indexing disk drive arm extending from the driver begins to travel along a curvilinearly extending groove that is interconnected to the radially extending groove in the indexing disk resulting in the rotation of the indexing disk. The rotation of the indexing disk also results in the sensor pack being rotated so that the next one of sensor cavities is positioned in alignment with the knife blade so that the sensor in the sensor cavity can be used for the next blood glucose test that is to be performed.

The dispensing instrument includes calibration circuitry with probes that contact a label on the sensor pack when the sensor pack is mounted on the indexing disk. The calibration circuitry provides the data processor with data as to the sensor pack and the tests performed with the sensors in the sensor pack.

BRIEF DESCRIPTION OF THE DRAWING

The present invention, together with the above and other objects and advantages, can best be understood from the following detailed description of the embodiment of the invention illustrated in the drawing, wherein:

FIGS. 9A–9C are exploded perspective views of the component parts of the sensor dispensing instrument of FIG. 1.

DETAILED DESCRIPTION OF THE PREFERRED EMBODIMENT

Figure 1:
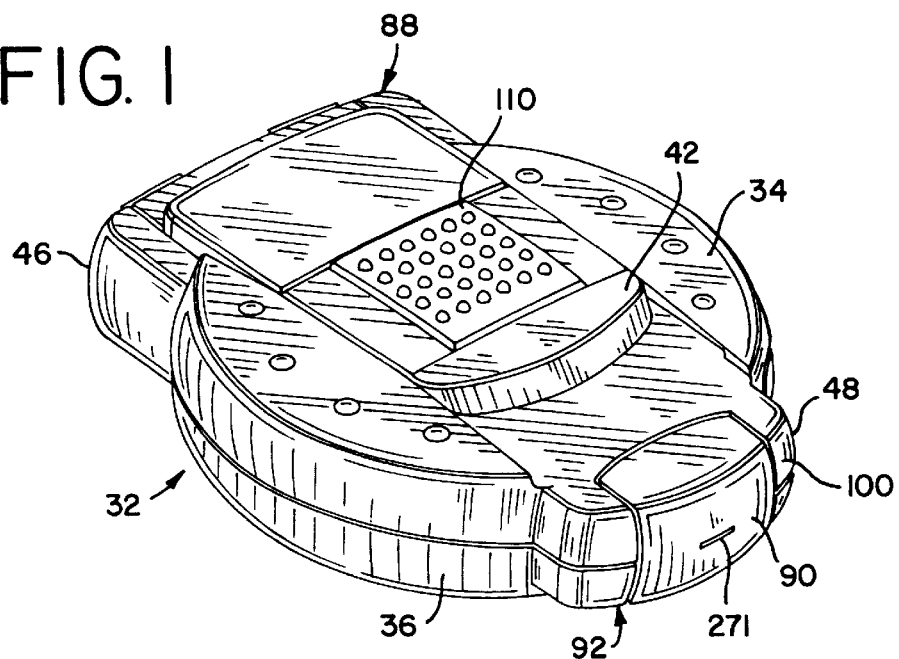
FIG. 1 is a perspective view of a blood glucose sensor dispensing instrument embodying the present invention.

Referring now more specifically to the drawings, therein is disclosed a blood glucose sensor dispensing instrument generally designated by the reference numeral 30 and embodying the present invention. The sensor dispensing instrument 30 includes an outer housing 32 having an upper case 34 and a lower case 36. The upper case 34 is pivotable with respect to the lower case 36 in a clam shell fashion so that a sensor pack 38 (FIGS. 5–8) can be positioned on an indexing disk 40 within the housing 32. With the sensor pack 38 so loaded in the housing 32, a slide actuator 42 on the upper case 34 of the housing 32 can be moved to engage a feed mechanism, generally designated by the numeral 44 (FIG. 9B), secured to the inside of the upper case 34 as the slide actuator 42 manually is pushed from a standby position (FIGS. 1–3) adjacent a rear end 46 of the upper case 34 toward an actuated or testing position (FIG. 4) adjacent a forward or testing end 48 of the upper case 34. The slide actuator 42 also can be moved to place the sensor dispensing instrument 30 in a data processing or display mode.

The feed mechanism 44 includes a driver 50 on which is pivotally mounted a knife blade assembly 52, from which extends an indexing disk drive arm 54 and on which is mounted a biasing spring 56. As the slide actuator 32 is moved toward its actuated position, the driver 50 with the knife blade assembly 52 thereon moves toward the testing end 48 and a button 58 at the distal end of the disk drive arm 54 travels in one of a plurality of radially extending grooves 60A–J in the indexing disk 40 such that the indexing disk 40 is not rotated while the driver 50 is being moved towards its testing position. As the knife blade assembly 52 is being moved toward the testing end 48, a knife blade 62 on the knife blade assembly 52 pierces a portion of a foil 64 covering one of a plurality of sensor cavities 66A–J, such as the cavity 66F, in a base portion 68 of the sensor pack 38 in alignment with the knife blade 62. A sensor 70 disposed in the cavity 66A is engaged by the knife blade 62 resulting in the knife blade 62 further severing the foil 64 covering the sensor cavity 66F and forcing or ejecting the sensor 70 out from the sensor cavity 66F.

Figure 4:
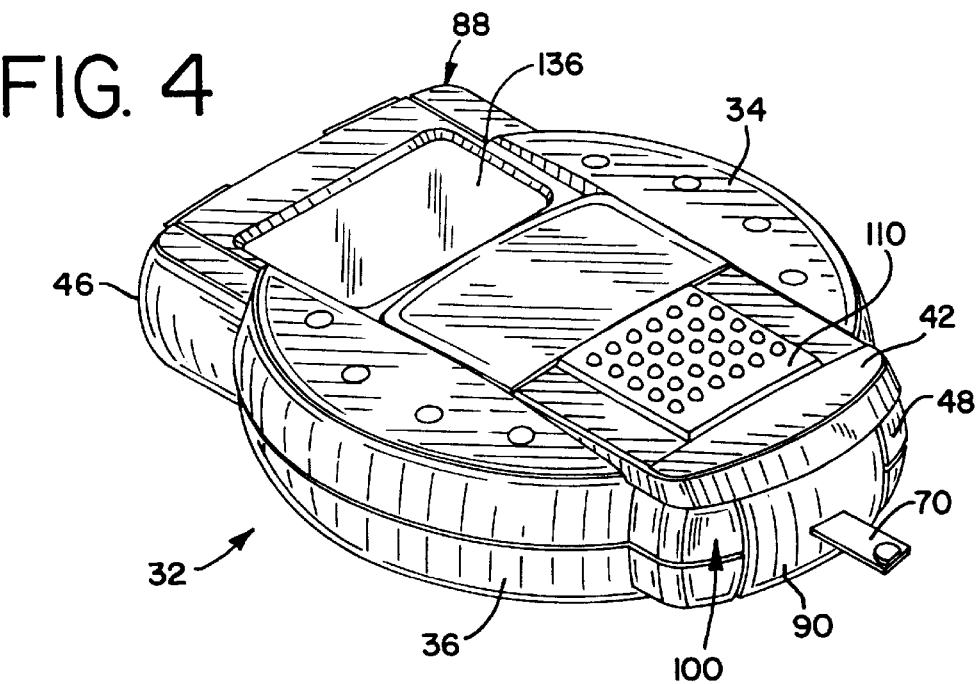
FIG. 4 is a perspective view of the blood glucose sensor dispensing instrument of FIG. 1 shown with a sensor in a testing position.

After the sensor 70 has been completely ejected from the sensor cavity 66F, the driver 50 engages a contact end 72 of a sensor actuator 74 that is forced against the sensor 70 to thereby maintain the sensor 70 in a testing position projecting out from the testing end 48 (FIG. 4). The sensor actuator 74 couples the sensor 70 to electronic circuitry on a printed circuit board 76 disposed in the upper case 34. The circuitry on the printed circuit board 76 may include a microprocessor or the like for processing, storing and/or displaying data generated during a blood glucose test procedure.

Once the blood analyzing test is completed, the slide actuator 42 is manually retracted in the opposite direction towards its standby position adjacent the rear end 46 of the upper case 34 and the sensor 70 is released from the contact end 72 of the sensor actuator 74 so that the sensor 70 can be removed from the housing 32. The driver 50 is similarly returned towards the rear end 46 such that the button 58 on the disk drive arm 54 begins to travel along one of a plurality of curvilinearly extending grooves 80A–J, such as groove 80A that is interconnected to the radially extending groove 60A, resulting in the rotation of the indexing disk 40. The rotation of the indexing disk 40 also results in the sensor pack 38 being rotated so that the next one of sensor cavities 66A–J is positioned in alignment with the knife blade 62 so that the sensor 70 in the next sensor cavity 66E can be used in the next blood glucose testing procedure.

As is best seen in FIGS. 1–4 and 9A–C, the upper case 34 and the lower case 36 of the sensor dispensing housing 32 are complementary, generally round in shape hollow containers that are adapted to be pivoted with respect to each other about pivot pins 82 extending outwardly in a rear section 84 of the lower case 36 into pivot holes 86 in a rear section 88 of the upper case 34. The upper case 34 and the lower case 36 are maintained in their closed configuration as shown in FIGS. 1–4 by a latch 90 that is pivotally mounted in a front or testing section 92 of the lower case 36 by pins 94 that extend inwardly into pivot holes 96 in the latch 90. When the latch 90 is pivoted upwardly, it clips into a recess 98 in a front or testing end section 100 of the upper case 34 thereby securing the upper case 34 and the lower case 36 in their closed configuration.

The upper case 34 has a recess 102 that extends in its exterior upper wall 104 from the front section 100 to adjacent the rear section 88. The slide actuator 42 is adapted to be mounted within the recess 102 so that side extending shoulders 106 slide within opposite grooves 108 along the edges of the recess 102. A slide latch 110 is held in position on the slide actuator 42 by a slide clip 112 that is positioned on the under side of the slide actuator 42, includes a clip 114 that extends through an opening 116 in the recess 102, clips onto the slide actuator 42 and has an mode actuator 118. The slide latch 110 includes a plurality of raised nubs 120 that provides a surface facilitating the movement of the slide latch 110 and the slide actuator 42 by a person using the sensor dispensing instrument 30.

Figure 2:
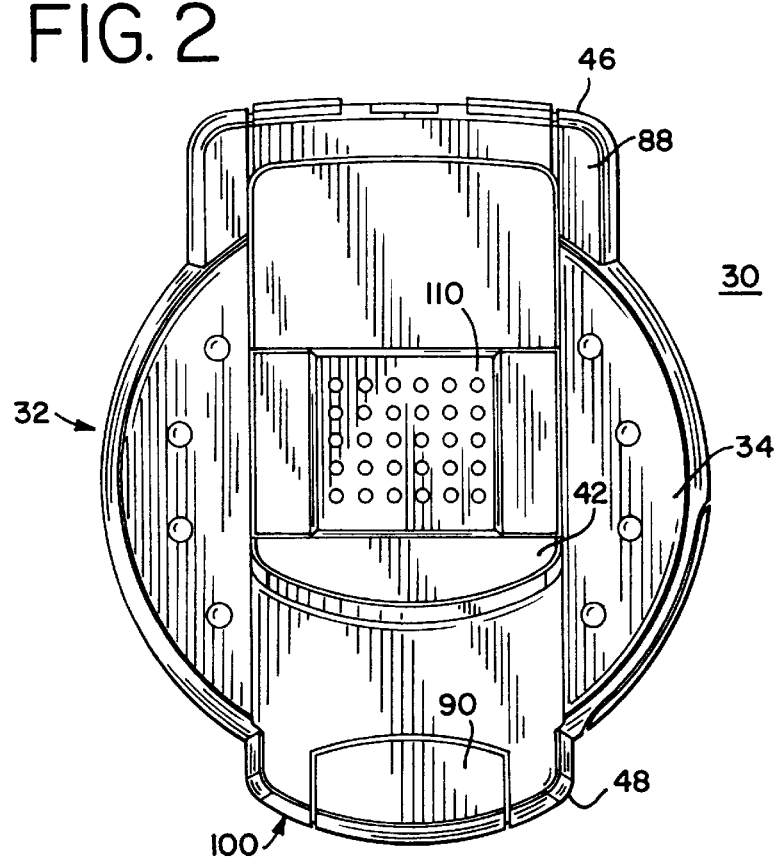
FIG. 2 is a top plan view of the blood glucose sensor dispensing instrument of FIG. 1.
Figure 3:
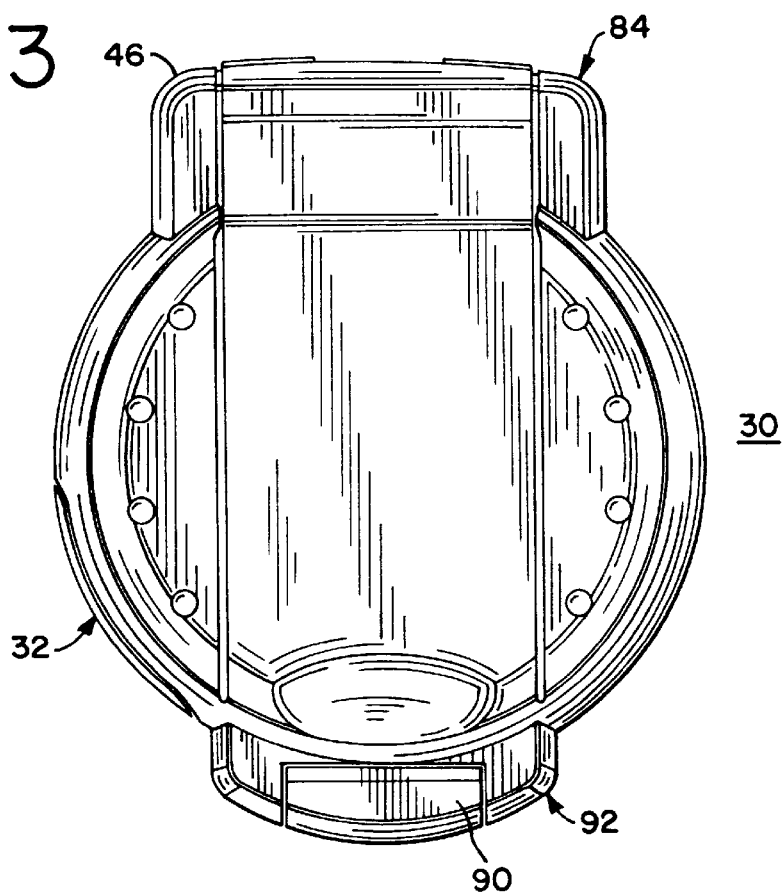
FIG. 3 is a bottom plan view of the blood glucose sensor dispensing instrument of FIG. 1.

The movement of the slide latch 110 places the instrument in one of two operating modes. In a first or testing mode, the slide latch 110 is positioned as shown in FIGS. 1, 2 and 4. In a second or data processing mode, the slide latch 110 is slid laterally with respect to the slide actuator 42.

When the slide latch 110 is in its testing mode position, a C-shaped catch 122 on the lower portion of the slide latch 110 is positioned in a longitudinal extending portion 124 of an opening 126 in the slide actuator 42 (see FIG. 9A). As is described hereinafter, the catch 122 projects through a slot 128 in the recess 102 so as to engage a post 130 extending upward from the driver 50 as the slide actuator 42 is moved toward the testing end 48. On the other hand, the C-shaped catch 122 on the lower portion of the slide latch 110 is disposed in a laterally extending portion 132 of the opening 126 so that the catch 122 moves within a slot 133 as the slide actuator 42 is moved toward the testing end 48 in the data processing mode of the sensor dispensing instrument 30. As a result, the catch 122 does not engage the post 130 when instrument 30 is in its data processing mode.

The upper case 34 includes a rectangular opening 134 in the rear section 88. A lens 136 is positioned in the opening 134 such that a liquid crystal display unit 138 attached below the lens 136 is visible through the lens 136 when the slide actuator 42 is moved away from the rear end 46 of the upper case 34. The liquid crystal display unit 138 is coupled to circuits on the printed circuit board 76 via connectors 140 and 142. The displays appearing on the liquid crystal display unit 138 when the instrument 30 is in its data processing or display mode are controlled by an actuating button 143 and a corresponding pad 144 and an actuating button 146 and a corresponding pad 147 that are disposed in the rear end 46. For example, the buttons 143 and 146 can be depressed to view and/or input the testing information that will be displayed on the liquid crystal display unit 138.

The upper case 34 also contains a battery holder 148 in which a pair of batteries 150 and 152 are disposed. The holder 148 is inserted into a side 149 of the upper case 34 adjacent the front section 100. When so inserted, the batteries 150 and 152 provide power for the electronics within the instrument 30 including the circuitry on the printed circuit board 76 and the liquid crystal display unit 138.

In order to place the instrument 30 in either its testing mode or its data processing or display mode, two actuating switches 154 and 156 are provided. Both of the switches 154 and 156 extend through openings 158 and 160 respectively in the recess 102. When the slide latch 110 is in its testing position and the slide actuator 42 is moved toward the testing end 48, the mode actuator 118 on the slide clip 112 will activate both of the switches 154 and 156 to thereby place the instrument 30 in its testing mode. On the other hand, the mode actuator 118 only will activate the switch 154 when the slide latch 110 is moved laterally to its display position and the slide actuator 42 is moved toward the front end 48. As a result, the instrument 30 will be in its display mode when only the switch 154 and not the switch 156 is actuated by the mode actuator 110, but in its testing mode when both of the switches 154 and 156 are activated.

Figure 9B:
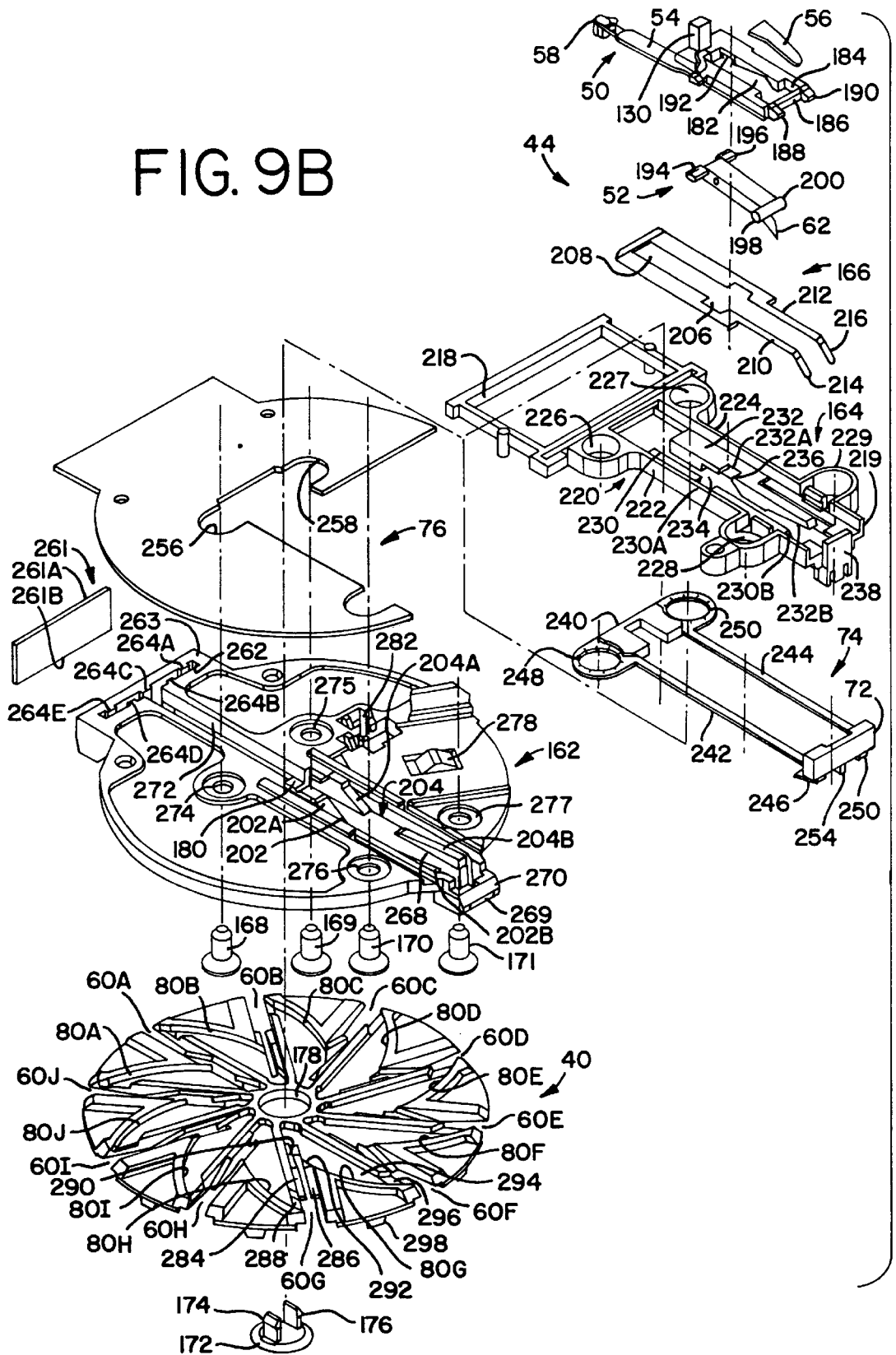
Figure 9C:
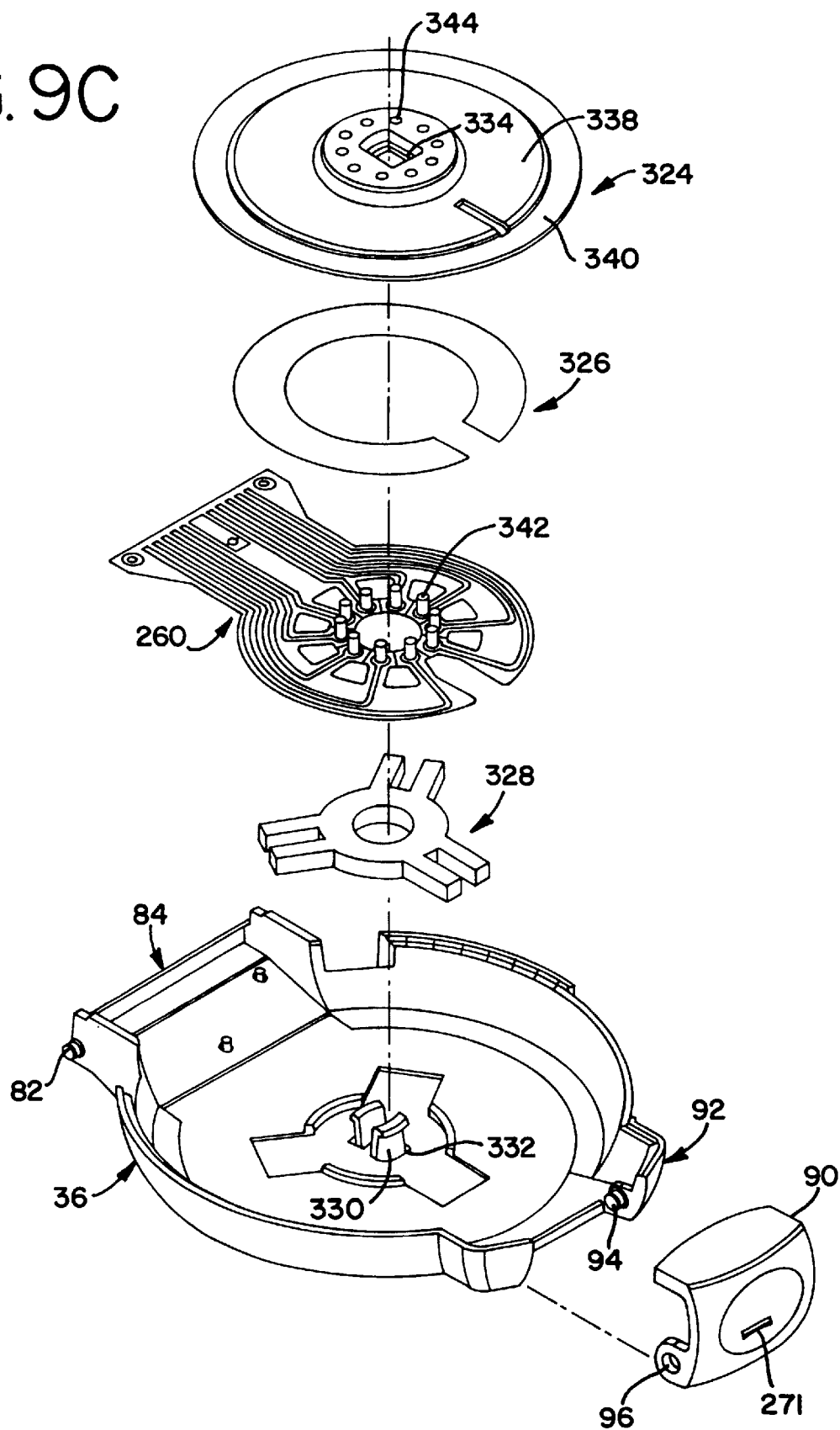

A block guide 162, the printed circuit board 76, the sensor actuator 74, a housing guide 164, a knife spring 166, the knife assembly 52 and the driver 50 are held together and secured to the upper case 34 by fasteners 168–171 that extend through those components and into the upper case 34 (see FIG. 9B). In addition, the indexing disk 40 is secured relative to the upper case 34 by being rotatably retained on the housing guide 164 by a retainer 172 that has a pair of latch arms 174 and 176 extending through a central hole 178 in the indexing disk 40 and latching into an opening 180 in the housing guide 164.

As previously indicated, the driver 50 is advanced toward the front or testing end 48 of the upper case 34 when the C-shaped clip 122 on the slide latch 110 engages the driver post 130 as the slide actuator 42 is advanced toward the testing end 48 by a person using the instrument 30. The driver 50 is a molded plastic component having a central recess 182 extending longitudinally to an enlarged recess 184 adjacent a forward edge 186 of the driver 50. A pair of cam projections 188 and 190 extend from the forward edge 186 and are adapted to engage the contact end 72 of the sensor actuator 74 as the driver 50 is pushed forwarded during a testing procedure. The driver 50 includes opposed recesses 192 extending outwardly from the recess 182 in which opposed pivot pins 194 and 196 on the knife blade assembly 52 are disposed. As a result, the knife blade assembly 52 is pivotably mounted on the driver 50 such that opposed cam followers 198 and 200 projecting from opposite sides of the knife blade assembly 52 can extend positioned through the enlarged recess 184 near the forward edge 186 of the driver 52. As will be discussed hereinafter, the cam followers 198 and 200 are adapted to travel along cam surfaces 202 and 204 formed on the block guide 162.

The driver 50 also includes the indexing disk drive arm 54 that extends rearwardly from the driver 50. The indexing disk drive arm 54 is made of spring type material such as stainless steel so that the button 58 affixed at the distal end of the arm 54 can travel in one of the radially extending grooves 60A–J in the indexing disk 40 when the driver 50 is being advanced toward the front end 48 or in one of the curvilinearly extending grooves 80A–J in the indexing disk 40 when the driver 50 is being returned toward the rear end 46 of the upper case 34.

In order to have the cam followers 198 and 200 extend through the recess 184, the biasing spring 56 is positioned on the driver 50 above the knife blade assembly 52 and exerts a downward force on the knife blade assembly 52. The cam followers 198 and 200 also will be extend through an enlarged recess 206 of a longitudinally extending slot 208 in the knife spring 166 when the recess 184 is in alignment with the recess 206. The knife spring 166 is positioned below the driver 50 and includes spring legs 210 and 212 on either side of the slot 208. The spring leg 210 has a ramp portion 214 and the spring leg 216 has a ramp portion 216. The cam followers 198 and 200 ride up onto the ramp portions 214 and 216 respectively as the driver 50 is being returned toward the rear end 46 to thereby lift the knife assembly 52 and in particularly the knife blade 62 away from the sensor pack 38 disposed on the indexing disk 40 as the knife assembly 52 is being returned toward the rear end 46 with the driver 50.

The driver 50 is mounted on the housing guide 164 which is secured to the block guide 162 such that the sensor actuator 74 and the printed circuit board 76 are sandwiched therebetween. The housing guide 164 includes a rear frame portion 218 in which the lens 136 and liquid crystal display unit 138 are disposed. A guide rail portion 220 extends from the rear frame portion 218 toward a front end 219 of the housing guide 164. The guide rail portion 220 has two forwardly extending rails 222 and 224 with fastening holes 226–229 located at the outer ends of the rails 222 and 224. The fasteners 168–171 extend respectively through the holes 226–229. The rail 222 has an upper cam track 230 and the rail 224 has an upper cam track 232. The cam track 230 has an opening 234 through which the cam follower 198 travels in entering the cam track formed by the cam tracks 230 and 202 and similarly the cam track 232 has an opening 236 through which the cam follower 200 travels in entering the cam track formed by the cam tracks 232 and 204. A sensor actuator guide 238 is disposed at the front end 219 of the housing guide 164 and assists in properly maintaining the position of the contact end 72 of the sensor actuator 74 relative to the sensor 70 when the sensor 70 is being used in test procedure.

The sensor actuator 74 is used to maintain the sensor 70 in its testing position and to couple the sensor 70 to circuitry on the printed circuit board 76. The sensor contact end 72 is connected to a circuit contact portion 240 by a pair of contact arms 242 and 244. The contact arms 242 and 244 are somewhat flexible being made of plastic molded over stainless steel. The stainless steel portion of the contact arm 242 is coupled between a sensor contact 246 extending from the sensor contact end 72 and a ring contact 248 in the circuit contact portion 240, the ring contact 248 in turn being coupled to circuits on the printed circuit board 76. Similarly, the stainless steel portion of the contact arm 244 is coupled between a sensor contact 250 extending from the sensor contact end 72 and a ring contact 252 in the circuit contact portion 240, the ring contact 252 in turn being coupled to circuits on the printed circuit board 76. When one of the sensors 70 is placed into a testing position (as, for example, shown in FIG. 4), the cam projections 188 and 190 extending from the forward edge 186 of the driver 50 cam against the contact end 72 of the sensor actuator 74 forcing the contact end 72 downwardly such that a post 254 on the sensor actuator 74 is forced against the sensor 70 to maintain the sensor 70 in its testing position. The post 254 also positions the underside of the contact end 72 the proper distance from the sensor 70 such that the sensor contacts 246 and 250 are deflected the correct amount to insure that the sensor contacts 246 and 250 make the desired contact with the sensor 70.

As previously indicated, the sensor actuator 74 couples the sensor 70 being used in a blood glucose test to circuitry on the printed circuit board 76. When the printed circuit board 76 is affixed on the block guide 162, the ring contacts 248 and 252 are coupled to contacts projecting into corresponding openings 256 and 258 on the printed circuit board 76. Circuitry on the printed circuit board 76 also is coupled to the liquid crystal display unit 138 through connectors 140 and 142. Circuitry on the printed circuit board 76 in addition needs to be coupled to a calibration circuitry 260 (FIG. 9C) that is located in the lower case 36 and that is used to determine information as to the sensor pack 38 being used in the instrument 30. In order to so couple the calibration circuitry 260 to circuitry on the printed circuit board 76, an elastomeric connector 261 is disposed in a channel 262 located in a rear end 263 of the block guide 162.

The elastomeric connector 261 is made of layers of silicon rubber extending from a top edge 261A to a bottom edge 261B with alternate layers having conductive materials dispersed therein to connect contacts on the top edge 261A to contacts on the bottom edge 261B. When the upper case 34 and the lower case 36 are closed, the connector 261 is compressed in the direction between the edges 261A and 261B such that the contacts along the top edge 261A engage circuitry on the printed circuit board 76 in the upper case 34 and the contacts along the bottom edge 261B engage the calibration circuitry 260 in the lower case 36. With the elastomeric connector 261 so compressed, low voltage signals can be readily coupled between the printed circuit board 76 and the calibration circuitry 260 through the connector 261. In view of the fact that the connector 261 needs to be compressed in the direction between the edges 261A and 261B and at the same time needs to remain in position in the channel 262 when the instrument 20 is opened, the channel 262 is formed in a serpentine configuration by rounded shaped ridges 264A–E extending inwardly into the channel 262. As seen in FIG. 9B, the ridges 264B and 264D extend inwardly from one side of the channel 262 in between the ridges 264A, 264C and 264E that extend inwardly from the opposite side of the channel 262. The serpentine configuration of the channel 262 enables the somewhat flexible connector 261 to be readily inserted into and maintained in the channel 262, but also allows the connector 261 to be compressed when the upper case 34 and the lower case 36 are closed.

The block guide 162 includes the cam tracks 202 and 204. The cam tracks 202 and 204 are in juxta-position with respect to the cam tracks 230 and 232 so as to form tracks therebetween through which the cam followers 198 and 200 respectively travel as the driver 50 is moved towards its testing position. The cam track 202 has a downwardly extending cam surface 202A that is adjacent a downwardly extending cam surface 230A of the cam track 230; the cam track 204 has a downwardly extending cam surface 204A that is adjacent a downwardly extending can surface 232A of the cam track 232; the cam track 202 has an upwardly extending cam surface 202B that is adjacent an upwardly extending cam surface 230B of the cam track 230; and the cam track 204 has an upwardly extending cam surface 204B that is adjacent an upwardly extending cam surface 232B of the cam track 232. As will be discussed hereinafter, the cam follower 198 rides along the cam surfaces 202A and 202B and the cam follower 200 rides along the cam surfaces 204A and 204B such that the knife blade 62 will protrude through a slot 268 in the block guide 162 between the cam tracks 202 and 204 and sever the portion of the foil 64 covering one of the sensor cavities 66A-J in alignment with the slot 268 when the sensor 70 is being ejected from that cavity into a testing position. When the sensor 70 is so ejected from the cavity, it will project through a sensor slot 269 in a sensor guide 270 at the front of the block guide 162 that is in alignment with a sensor slot 271 in the latch 90.

Another slot 272 extends rearwardly towards the rear edge 263 of the block guide 162. The slot 272 is designed such that the indexing disk drive arm 54 and the button 58 on the distal end of the arm 54 can move through the slot 272 in the grooves 60A-J and 80A-J on the indexing disk 40 as the driver 50 is moved forward, then backward during a testing procedure.

The block guide 162 includes mounting holes 274–277 through which the fasteners 168–171 respectively extend in order to mount the block guide 162 in proper position in the upper case 34. When the block guide 162 is so positioned in the upper case 34, a flexible battery contact 278 in the block guide 162 is coupled to the batteries 150 and 152 in the battery holder 148 through an opening 280 in the battery holder 148. This battery contact 278 is coupled to flexible electrical contacts 282 extending from the block guide 162 that make contact with and provide power to the circuitry on the printed circuit board 76. The block guide 162 also provides support surfaces 283 and 284 for the contact arms 242 and 244 of the sensor actuator 74.

As previously indicated, the indexing disk 40 is mounted on the block guide 162 by the retainer 172. In so mounting the indexing disk 40, the indexing disk 40 is rotatable with respect to the block guide 162. When the driver 50 is being moved toward the front end 46 of the upper case 34 in order to place one of the sensors 70 in a testing position, the button 58 on the indexing disk drive arm 54 travels in one of the radially extending grooves 60A–J. As is illustrated with respect to the groove 60G in FIG. 9B, each of the grooves 60A–J has upwardly inclined cam surfaces 285 and 286 positioned on opposite sides of a knife slot 288. As the button 58 on the indexing disk drive arm 54 travels within the groove 60G, the button 58 rides on the cam surfaces 285 and 286 due to the downward force exerted by the indexing disk drive arm 54 which is flexed slightly upward as the button 58 rides upward on the cam surfaces 285 and 286. The cam surfaces 285 and 286 form steps 290 and 292 between the radially extending groove 60G and the interconnected curvilinearly extending groove 80G. The steps 290 and 292 insure that the button 58 will travel only in the radially extending straight grooves 60A–J as the driver 50 is being moved forward toward the front end 48 and not in the radially extending straight grooves 60A–J when the driver 50 is being moved rearwardly toward the rear end 46. This is because the button 58 will snap down into the curvilinearly extending groove 80G as it travels past the steps 290 and 292 and the steps 290 and 292 prevent the button 58 from traveling back into the groove 60G as the driver 50 is being returned toward the rear end 46. The knife slot 288 in the grooves 60A–J enable the knife blade 62 to extend through the indexing disk 40 and sever the foil 64 overlying one of the sensor cavities 66A–J that is in alignment and beneath a particular one of the grooves 60A–J.

The grooves 60A–J are straight, radially extending grooves and as a result, the indexing disk 40 is not rotated as the button 58 travels within one of the grooves 60A–J. On the other hand, the button 58 will travel along one of the curvilinearly extending grooves 80A–J as the driver 50 is being returned to its standby position or towards the rear end 46. Due to the fact that the grooves 80A–J are curved, the indexing disk 40 will be rotated as the button 58 is pushed within the grooves 80A–J so that the next straight groove (such as the groove 60F) will be in alignment with the next one of the sensor cavities 66A–J when the driver 50 is returned to its standby position towards the rear end 46.

As is illustrated in FIG. 9B with respect to groove 80G, the grooves 80A–J have a downwardly inclined surface 294 such that a step 296 is formed between the groove 80G and the next straight groove 60F. The step 296 insures that the button 58 will not travel in the curvilinearly extending grooves 80A–J as the driver 50 is being moved forward toward the front end 48. This is because the button 58 will snap down into the straight groove 60F as it travels past the step 296 and the step 296 prevents the button 58 from traveling back into the groove 80G as the driver 50 is being moved toward the front end 48.

The indexing disk 40 has ten notch retainers 298 extending along the outer peripheral edge of the bottom surface of the indexing disk 40. Each of the notch retainers 298 is adapted to be positioned in one of the notches 300 formed along the outer perimeter of the foil 64 and a corresponding one of the notches 302 along the outer perimeter of the base portion 68 of the sensor pack 38 when the sensor pack 38 is positioned below the indexing disk 40. When the notch retainers 298 are positioned in the notches 300 and 302, the sensor pack 38 is retained on the indexing disk 40 so that the sensor cavities 66A–J are in alignment respectively with the grooves 60A–J in the indexing disk 40. Hence, the notch retainers 298 and the notches 300 and 302 have the dual purpose of retaining the sensor pack 38 on the indexing disk 40 so that the sensor pack 38 will rotate with the indexing disk 40 and of positioning the sensor pack 38 in proper circumferential alignment relative to the indexing disk 40.

Figure 5:
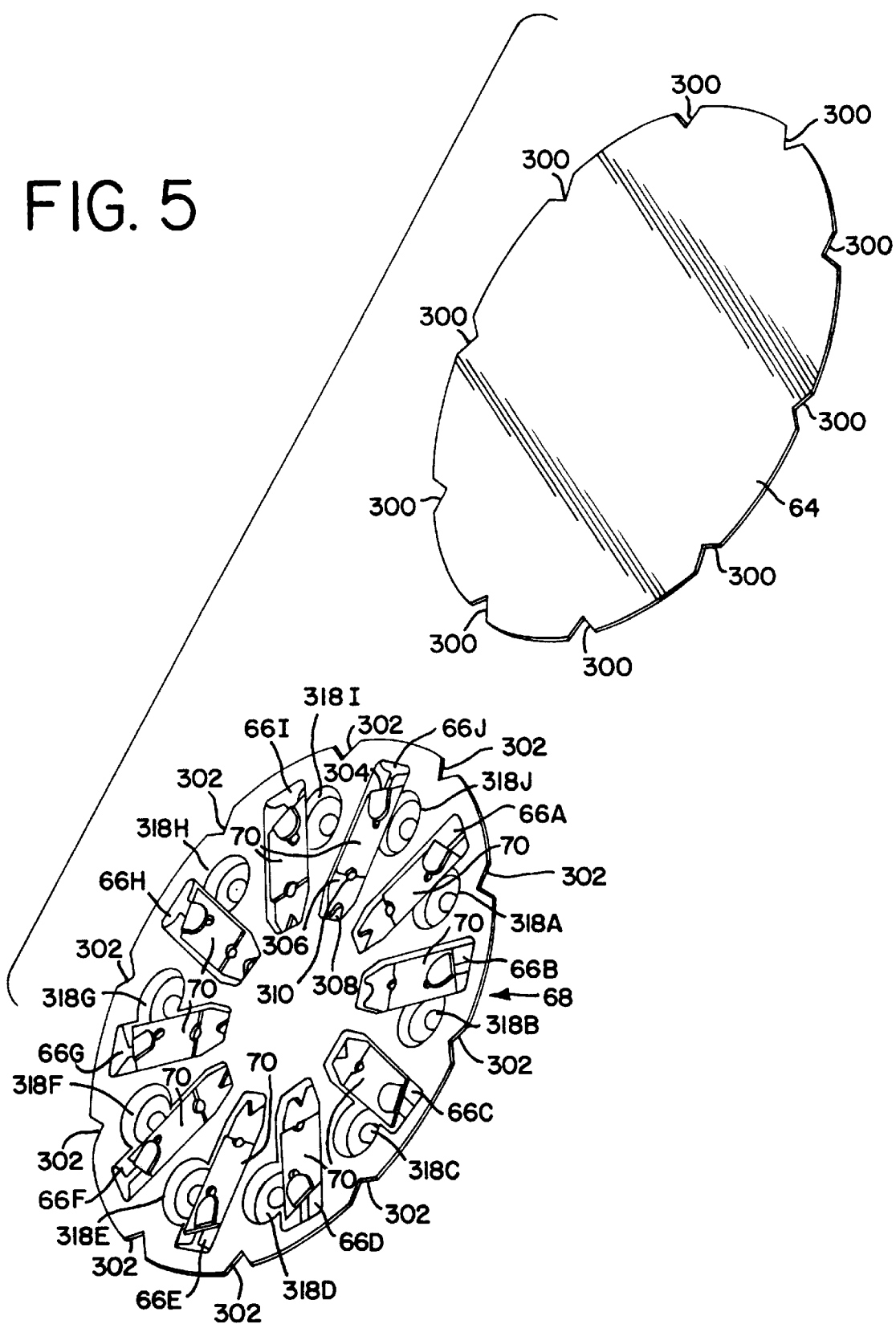
FIG. 5 is an exploded perspective view of a sensor pack used in the blood glucose sensor dispensing instrument of FIG. 1 with the foil portion of the sensor pack separated from the base portion of the sensor pack.
Figure 6:
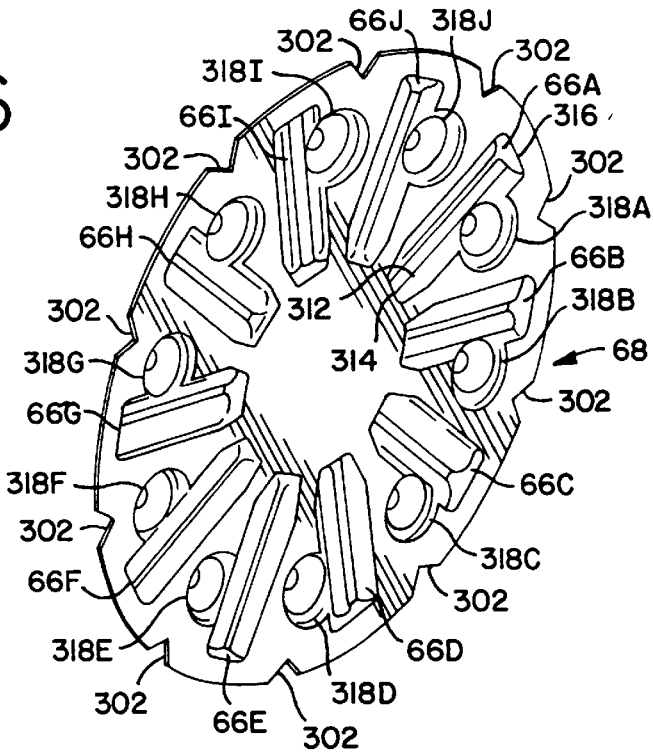
FIG. 6 is top view of the base portion of the sensor pack of FIG. 5.
Figure 7:
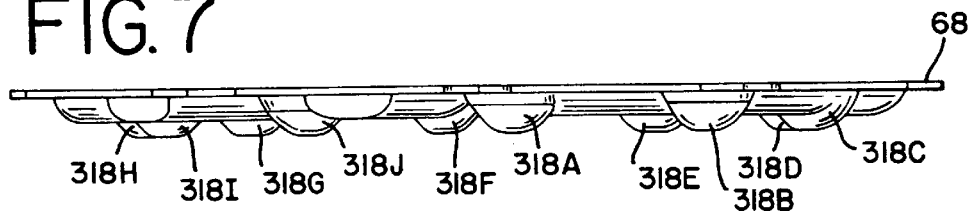
FIG. 7 is side view of the base portion of the sensor pack of FIG. 5.

The sensor pack 38 that is positioned below the indexing disk 40 is adapted to house ten sensors 70 with one of the ten sensors 70 in each of the sensor cavities 66A–J. As is illustrated in FIG. 5 with respect to the sensor 70 in the sensor cavity 66J, each of the sensors 70 has a generally flat, rectangular shape extending from a front or testing end 304 to a rear end 306. The front end 304 is angled so that the front end 304 is adapted to puncture an unsevered portion of the foil 64 overlying the sensor cavity 66J as the sensor 70 is being forced out of the sensor cavity 66J by the knife blade 62 and is adapted to be placed into blood that is being analyzed. The rear end 306 of the sensor 70 includes a small notch 308 into which the knife blade 62 will become disposed as the knife blade 62 is ejecting the sensor 70 from the sensor cavity 66J. The notch 308 provides a target area for the knife blade 62 to contact the sensor 70 and once the knife blade 62 is in contact with the notch 308, the sensor 70 becomes centered on the knife blade 62. Contacts 310 near the rear end 306 of the sensor 70 are adapted to mate with sensor contacts 246 and 250 on the contact end 72 of the sensor actuator 74 when the sensor 70 is in the testing position illustrated in FIG. 4. As a result, the sensor 70 is coupled to the circuitry on the printed circuit board 76 so that information generated in the sensor 70 during testing can be stored and/or analyzed.

Each of the sensors 70 is provided with a capillary channel that extends from the front, testing end 304 of the sensor 70 to biosensing or reagent material disposed in the sensor 70. When the testing end 304 of the sensor 70 is placed into fluid (for example, blood that is accumulated on a person's finger after the finger has been pricked), a portion of the fluid is drawn into the capillary channel by capillary action so that a sufficient amount of fluid to be tested is drawn into the sensor 70. The fluid then chemically reacts with the reagent material in the sensor 70 so that an electrical signal indicative of the blood glucose level in the blood being tested is supplied to the contacts 310 and thereby through the sensor actuator 74 to the printed circuit board 76.

The sensor pack 38 is formed of the circularly shaped base portion 68 and the correspondingly configured foil 64. The sensor cavities 66A–J are formed as depressions in the base portion 68 with each of the sensor cavities 66A–J adapted to house one of the sensors 70. As illustrated with respect to the sensor cavity 66A in FIG. 6, each of the sensor cavities 66A–J has a bottom support wall 312 that extends from an inner end 314 to an outer end 316 of the sensor cavity 66A. The support wall 312 is inclined or sloped slightly upward as it extends from the inner end 314 to the outer end 316. This sloping of the support wall 312 results in the sensor 70 being raised slightly as it is being ejected from the sensor cavities 66A–J so that it will avoid or pass above that portion of the heat seal affixing the foil 64 to the base portion 68 along the outer peripheries of the foil 64 and the base portion 68.

Each of the sensor cavities 66A–J is in fluid communication with a corresponding one of desiccant cavities 318A–J. Each of the desiccant cavities 318A–J is formed of a small depression in the base portion 68 adjacent the corresponding one of the sensor cavities 66A–J. Desiccant material is disposed in the desiccant cavities 318A–J in order to insure that the sensor cavities 66A–J are maintained at an appropriate humidity level so that the reagent material in the sensor 70 disposed in the particular sensor slot 66A–J is not adversely affected prior to being used. The desiccant material might be in the form of a small bag or round bead of material or any other form that can be readily disposed in the desiccant cavities 318A–J. The amount of such desiccant material placed in each of the desiccant cavities 318A–J will be dependent on the amount that is required to maintain the sensor cavities 66A–J in a desiccate state. One type of desiccant material that could be used is sold under the trademark NATRASORB and is available in powder, pellet and bead forms.

The notches 302 are formed along the outer peripheral edge of the base portion 68. When the foil 64 is sealed to the base portion 68, the notches 300 along the outer peripheral edge of the foil 64 will be in alignment with the notches 302 to thereby form an integral series of notches along the outer peripheral edge of the sensor pack 38. Each of the notches formed by the notches 300 and 302 is associated with one of the sensor cavities 66A–J in the base portion 68 such that when the sensor pack 38 is mounted on the indexing disk 40 with the notch retainers 298 disposed in the notches 300 and 302, the sensor cavities 66A–J will each be in proper alignment with an individual one of the straight grooves 60A–J in the indexing disk 40.

The foil 64 is adapted to cover the top of the base portion 68 and be affixed to the base portion by heat sealing along the entire outer peripheral edge of the foil 64 to the outer peripheral edge of the base portion 68. The foil 64 also is heat sealed about the entire perimeter of each set of the sensor retaining cavities 66A–J and the desciccant cavities 318A–J to seal the sensor retaining cavities 66A–J and the desiccant cavities 318A–J such that the individual sensors 70 are maintained in a desiccated state and isolated from each other. As a result, the opening of one of the sensor cavities 66A–J will not affect the desiccated state of any of the other sensor cavities 66A–J. The foil 64 may be made of any material that will adequately seal the sensor cavities 66A–J and the desiccant cavities 318A–J while providing a material that will can be really severed by the knife blade 62 and pierced by the sensor 70 as it is being pushed out from the sensor cavities 66A–J. One type of foil that can be used for the foil 64 is AL-191-01 foil distributed by Alusuisse Flexible Packaging, Inc.

Figure 8:
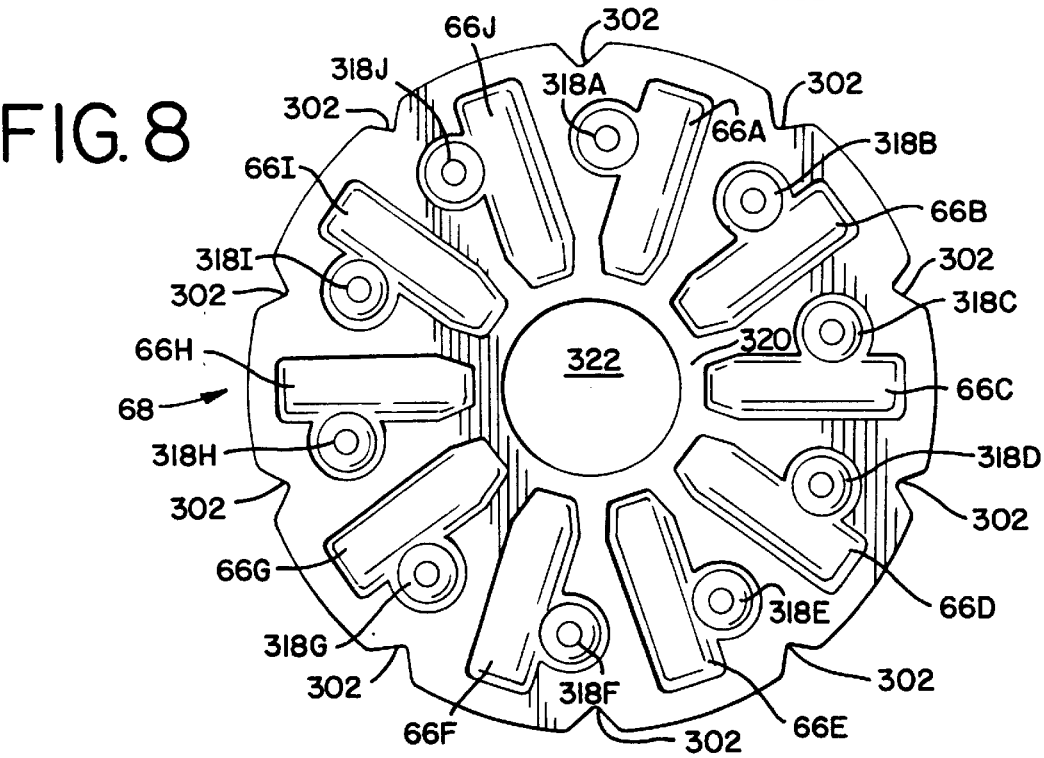
FIG. 8 is bottom view of the base portion of the sensor pack of FIG. 5.

As is illustrated in FIG. 8, the base portion 68 includes a label area 320 on its underside inwardly of the sensor cavities 66A–J. A conductive label 322 is positioned in this label area 320 and provides calibration and production information that can be sensed by the calibration circuitry 260.

The calibration circuitry 260 is located in the lower case 36. The calibration circuitry 260 as well as an upper plate 324, an adhesive ring 326 and a pad 328 are held in position in the lower case 36 by a retainer clip 330 that extends through an opening 332 in the lower case 36 and into an opening 334 in the upper plate 324. The upper plate 324 has an inner metal region 338 with the remaining outer portions 340 being plastic. The calibration circuitry 260 is maintained in proper circumferential position with respect to the upper plate 324 by the adhesive ring 326 such that probes 342 extending upperwardly from the calibration circuitry 260 are in alignment with and extend through holes 344 in the inner metal region 338 about the opening 334.

When the sensor dispensing instrument 30 is closed with the lower case 36 latched to the upper case 34 by the latch 90, the probes 342 make contact with the conductive label 322 located in the label region 320 of the sensor pack 38 being used in the sensor dispensing instrument 30. In order to assure that the probes 342 press against the conductive label 322 with an appropriate force, the pad 328 is positioned below the flexible calibration circuitry 260 and provides a cushion so that the probes 342 can move independently with respect to each other particularly as the sensor pack 38 is being rotated by the indexing disk 40. As a result, information, such as calibration and production data, contained on the label 322 can be transmitted via the probes 342 to the calibration circuitry 260 which in turn couples the data to the circuitry on the printed circuit board 76 via the elastomeric connector 261. The information then can be displayed on the liquid crystal display unit 138 through the lens 136 when the sensor dispensing instrument 30 is placed in its display mode by the movement of the slide latch 110 laterally and forward movement of the slide actuator 42 toward the front end 48.

In order for the sensor dispensing instrument 30 to be used by a person for testing of blood glucose, the instrument 30 needs to be opened so that the sensor pack 38 can be inserted in proper position on the indexing disk 40. The instrument 30 is opened by moving the latch 90 away from its latching position in the recess 98 in the front section 100 of the upper case 34. With the latch 90 so released, the lower case 36 can be swung away from the upper case 34 about the pivot pins 82. Any previously used sensor pack 38 can be removed from its position on the indexing disk 40 and a new sensor pack 38 can be positioned on the indexing disk 40 by positioning the notch retainers 298 in the notches 300 and 302 along the outer periphery of the sensor pack 38. With the sensor pack 38 so positioned on the indexing disk 40, each of the sensor cavities 66A–J will be in alignment beneath the knife slot 288 in one of the straight radially extending grooves 60A–J.

With the sensor pack 38 positioned on the indexing disk 40, the lower case 36 can be swung toward the upper case 34. The latch 90 is pivoted on the pins 94 and is latched in the recess 98 in the front section 100 of the upper case 34 such that the lower case 36 is closed against the upper case 34. When the lower case 36 and the upper case 34 are latched together, the probes 342 projecting from the calibration circuitry 260 through the holes 344 in the upper plate 324 engage the label 322 located in the label area 320 of the sensor pack 38. As a result, information contained on the label 322 with respect to the sensor pack 38 is provided to the circuitry on the printed circuit board 76 via the connector 261. In addition, the position of the sensor pack 38 can be detected by the probes 342 so that the rotational position of the sensor pack 38 can be detected as the sensors 70 in the sensor pack 38 are used for testing purposes.

With the upper case 34 and the lower case 36 latched together, the slide latch 110 can be manipulated to place the sensor dispensing instrument 30 in either its display or data processing mode or its testing mode. For example, the slide latch 110 can be moved laterally with respect to the longitudinal axis of the instrument 30 to place the instrument 30 in its display mode. As the slide latch 110 is moved laterally, the C-shaped catch 122 is moved into the laterally extending portion 132 of the opening 126 in the slide actuator 42. The movement of the slide actuator 42 toward the front end 48 results in a cam surface 346 on the mode actuator 118 on the side of the slide clip 112 contacting and depressing an actuator button 348 of the on/off switch 154 extending through the opening 158 to thereby close the normally open switch 154. With the slide latch 110 moved laterally, the mode actuator 118 will not contact an actuator button 350 of the on/off switch 156 that extends through the opening 160. The closing of the on/off switch 154 without the actuation of the on/off switch 156 results in the sensor dispensing instrument 30 being activated into its display mode. During this forward movement of the slide actuator 42 toward the front end 48, the C-shaped catch 122 will move in the slot 133 so that it will not engage the post 130 extending from the driver 50. As a result, the driver 50 will remain in its standby position toward the rear end 46 of the upper case 34.

As the slide actuator 42 is moved toward the front end 48, the slide actuator 42 will be moved away from the opening 134 in the rear section 88 of the upper case 34 and the liquid crystal display unit 138 will be visible through the lens 136. Information concerning the sensor pack 38 and the tests that have been conducted can be displayed on the liquid crystal display unit 138. The information that is displayed can be determined by the actuation of the buttons 143 and 146 projecting from the rear end 46 of the upper case 34. The buttons 143 and 146 also are used to input information into the circuitry on the printed circuit board 76 in accordance with the displays on the liquid crystal display unit 138. As this information is being displayed or inputted, an audible indicator is selectively annunciated by a piezo alarm 352 located adjacent the switches 154 and 156 in the upper case 34.

When the user of the sensor dispensing instrument 30 has completed obtaining information or inputting data, the slide actuator 42 is returned toward the rear end 46 of the upper case 34 by sliding it in the recess 102 formed in the upper wall 104 of the upper case 34. After the mode actuator 118 has passed the actuator button 348, the actuator button 348 will no longer be depressed and the on/off switch 154 will be returned to its normal open condition. The instrument 30 will then be in its off or standby condition. Once the slide actuator 42 has been returned to its full retracted position, the slide actuator 42 will be held in that position by a detent 354 projecting from the recess 102 adjacent the rear end of the slot 133. With the slide actuator 42 in its fully retracted position, the slide actuator 42 will again cover the lens 136 for the liquid crystal display unit 138 and the slide latch 110 can be moved laterally back to its normal position as illustrated in FIG. 1 of the drawings.

The primary use of the sensor dispensing instrument 30 is in connection with a blood glucose test. When such a test is to be conducted, a user of the instrument 30 can push against the nubs 120 on the slide latch 110 in order to slide the slide actuator 42 in the recess from its standby position near the rear end 46 toward the front or testing end 48. As the slide actuator 42 is moved toward the testing end 48, the cam surface 346 on the mode actuator 118 on the side of the slide clip 112 contacts and depresses the actuator button 348 of the on/off switch 154 extending through the opening 158 and the actuator button 350 of the on/off switch 156 extending through the opening 160. The depression of both of the actuator buttons 348 and 350 by the mode actuator 118 closes both of the on/off switches 154 and 156. The closing of both of the on/off switches 154 and 156 results in the sensor dispensing instrument 30 being activated into its testing mode.

As the slide actuator 42 is moved toward the front end 48, the C-shaped catch 122 will move in the slot 128 so that it will be in engagement with the post 130 extending from the driver 50. As a result, the driver 50 will be moved along with the slide actuator 42 toward the front end 48. When the driver 50 was in its standby position toward the rear end 46, the cam follower 198 was extended through the enlarged recess 184 in the driver 50, the enlarged recess 206 in the knife spring 166, and the opening 234 in the housing guide 164 and similarly the cam follower 200 was extended through the enlarged recess 184 in the driver 50, the enlarged recess 206 in the knife spring 166, and the opening 236 in the housing guide 164. Consequently, the cam followers 198 and 200 were posed at the rear end of the cam surfaces 202A and 204A respectively of the cam tracks 202 and 204.

As the driver 50 is moved toward the front end 48 with the slide actuator 42, the cam followers 198 and 200 respectively will travel along the downwardly extending cam surfaces 202A and 204A such that the knife blade 62 will dip through the slot 268 in the block guide 162 between the cam tracks 202 and 204 and the knife slot 288 in the straight groove, for example, the groove 60J, on the indexing disk 40 in alignment with the slot 268. The continued downward movement of the knife blade 62 as the cam followers 198 and 200 travel along the cam surfaces 202A and 204A respectively results in the knife blade 62 beginning to sever a portion of the foil 64 that is covering the particular one of the sensor cavities 66A–J, for example, the sensor cavity 66J, that is in alignment with the groove 60J on the indexing disk 40.

As the knife blade 62 severs the foil 64, it also dips further into the sensor cavity 66J and engages the notch 308 at the rear end 306 of the sensor 70 housed in the sensor cavity 66J. The further movement of the driver 50 and thereby the knife blade 62 toward the front end 48 causes further severing of the foil 64 over the sensor cavity 66J and the front end 304 of the sensor 70 will begin to ride upwardly on the inclined bottom support wall 312. As this is occurring, the cam follower 198 will start to travel along the upperwardly inclined cam surface 202B and the cam follower 200 will start to travel along the upperwardly inclined cam surface 204B such that the knife blade 62 will tend to lift the sensor 70 as it is being ejected from the cavity 66J with the front end 304 piercing through the portion of the foil 64 overlying the sensor cavity 66J. The front edge 304 of the sensor 70 has a pointed, biased geometry so that the front edge 304 of the sensor 70 cuts an exit hole through the foil 64 rather than merely stretching it as the sensor 70 is bursting through the foil 64 covering the sensor cavity 66J. The lifting of the front end 304 due at least in part to the upwardly inclined support wall 312 enables the front end 304 of the sensor 70 to avoid the heat seal around the outer peripheries of the foil 64 and the base portion 68 of the sensor pack 38; otherwise the heat seal could interfere with the ejection of the sensor 70 from the sensor cavity 66J.

The continued forward movement of the driver 50 with the slide actuator 42 will result in the sensor 70 being completely ejected from the sensor cavity 66J. Once the sensor 70 has been ejected from the sensor cavity 66J, the sensor 70 is guided into the sensor slot 269 in the sensor guide 270 and the aligned sensor slot 271 in the latch 90 until the front or testing end 304 of the sensor 70 is projecting out from the front end 48 of the upper case as is illustrated in FIG. 4. As the sensor 70 is being guided through the sensor slots 269 and 271, the cam projections 188 and 190 projecting from the forward edge 186 of the driver 50 engage the contact end 72 of the sensor actuator 74 thereby forcing the contact end 72 downwardly along the sensor actuator guide 238 toward the sensor 70. The post 254 extending from the contact end 72 is forced against the sensor 70 to maintain the sensor 70 in the sensor guide 270 and projecting through the sensor slots 269 and 271. In addition, flexible sensor contacts 246 and 250 projecting from the contact end 72 on either side of the post 254 make electrical contact with the contacts 310 on the sensor 70 so that the contacts 310 on the sensor 70 are coupled to the circuits on the printed circuit board 76 through the contacts 246 and 250, the contact arms 242 and 244 of the sensor actuator 74, and the ring contacts 248 and 252 on the circuit contact portion 240 of the sensor actuator 74. The engagement of the post 254 against the sensor 70 not only clamps the sensor 70 in its testing position, but also assures that the sensor contacts 246 and 250 make the desired contact with the sensor contacts 310 by positioning the contact end 72 of the sensor actuator 74 the appropriate distance from the sensor 70.

As the driver 50 is being moved forward toward the front end 48 of the upper case 34, the button 58 at the distal end of the indexing disk drive arm 54 will travel through the slot 272 in the block guide 162 and along the straight groove 60E in the indexing disk 40 (i.e., the groove diametrically opposite to the groove 60J). The indexing disk 40 will not be rotated as the button 58 travels along the cam surfaces 285 and 286 in the groove 60E and past the steps 290 and 292 into the interconnected curvilinearly groove 80E.

Once the sensor 70 is in its testing position and the slide actuator 42 and the driver 50 have been moved to their forward or testing position, the button 58 is positioned in the innermost portion of the curvilinearly groove 80E and the cam followers 198 and 200 are positioned forward of the ramp portions 214 and 216 of the knife spring 166. The testing end 304 of the sensor 70 then can be placed into fluid, such as blood that is accumulated on a person's finger after the finger has been pricked. The fluid is absorbed into the sensor 70 and chemically reacts with the reagent material in the sensor 70 so that an electrical signal indicative of the blood glucose level in the blood being tested is supplied to the contacts 310 and thereby through the sensor actuator 74 to the printed circuit board 76.

Once the blood analyzing test is completed, the slide actuator 42 is moved away from the front end 48 toward the rear end 46 of the upper case 34 by a user of the instrument 30 pushing on the nubs 120 projecting from the slide release 110. As the slide actuator 42 is moved toward the rear end 46, the cam projections 188 and 190 projecting from the forward edge 186 of the driver 50 are moved away from engaging the contact end 72 of the sensor actuator 74 so that the contact end 72 is moved away from the sensor 70 due to the resiliency in the contact arms 242 and 244 as they extend forward of the support surfaces 283 and 284 on the block guide 162. With the post 254 no longer forced against the sensor 70, the sensor 70 that was used in the glucose test can be removed from the sensor slots 269 and 271 and discarded.

As the driver 50 is being moved away from the front end 48, the cam follower 198 on the knife assembly 52 will ride up the ramp portion 214 onto the spring leg 210 of the knife spring 166 and the cam follower 200 on the knife assembly 52 will ride up the ramp portion 216 onto the spring leg 212 of the knife spring 166. The knife spring 166 pivots the knife assembly 52 upward about the pivot pins 194 and 196 so that the knife blade 62 is displaced from the indexing disk 40 and the sensor pack 38 mounted therebelow. With the knife blade 62 so displaced from the indexing disk 40, the indexing disk 40 can be rotated in order to place another one of the sensor cavities 66A–J in alignment with the slot 268 in the block guide 162.

In this regard, the retraction of the slide actuator 42 toward the rear end 46 forces the button 58 on the indexing disk drive arm 54 to travel along the downwardly inclined surface 294 in the groove 80E. This movement in the curved groove 80E causes the disk 40 to be rotated such that the next straight groove 60I will be moved into alignment under the slot 272 in the block guide 162 as the button 58 enters the next straight groove 60D. Once the slide actuator 42 reaches its fully retracted position past the detent 354, the biasing spring 56 forces the knife blade assembly 52 downwardly so that the cam follower 198 is extended through the enlarged recess 184 in the driver 50, the enlarged recess 206 in the knife spring 166, and the opening 234 in the housing guide 164 and similarly the cam follower 200 is extended through the enlarged recess 184 in the driver 50, the enlarged recess 206 in the knife spring 166, and the opening 236 in the housing guide 164. As a result, the cam followers 198 and 200 are posed at the rear end of the cam surfaces 202A and 204A respectively of the cam tracks 202 and 204 so that another one of the sensors 70 in the sensor pack 38 can be ejected from the sensor pack 38 and used in another testing procedure.

While the invention has been described with reference to details of the illustrated embodiment, these details are not intended to limit the scope of the invention as defined in the appended claims. For example, the instrument 30 can be used for testing fluids other than blood glucose. In fact, the instrument 30 can be used in connection with analyzing any type chemistry fluid that can be analyzed by means of a reagent material.

What is claimed and desired to be secured by Letters Patent of the United States is:

1. A method of handling a plurality of fluid sensors comprising:

installing a sensor pack on an indexing mechanism disposed in a housing of a sensor dispensing instrument such that one of a plurality of sensor retainers that is enclosed by an enclosure and that accommodates one of said plurality of fluid sensors is in a feed position;

actuating a feed actuator from an actuator standby position, said feed actuator being associated with said indexing mechanism and is adapted to advance a driver that is pivotable with respect to said sensor pack, said driver piercing a portion of said enclosure and engaging said sensor disposed within said sensor retainer so that said sensor in said sensor retainer is advanced out of said sensor retainer into a testing position as said feed actuator is advancing from said actuator standby position; and returning said feed actuator to said actuator standby position so as to return said driver to a driver standby position, said driver being pivoted away from said sensor pack as said feed actuator is so returned to said actuator standby position and said indexing mechanism being simultaneously advanced as said actuator is being returned to said actuator standby position such that another one of said plurality of sensor retainers is moved into said feed position as said feed actuator is being returned to said actuator standby position.

2. A method of handling a plurality of fluid sensors as set forth in claim 1 wherein said sensor pack includes a base portion in which said sensor retainers are formed, wherein said enclosure is a foil that is heat sealed on said base portion about an outer peripheral edge of said base portion and about each of said sensor retainers to seal said sensor retainers with said sensors therein, and wherein each of said sensor retainers includes a sensor cavity having a support wall on which said sensor is disposed that extends in a radial direction from adjacent the peripheral edge of said base portion toward a center of said base portion, said support wall having a sloped portion that is sloped toward said foil in a direction toward said peripheral edge of said base portion, said method further including advancing said sensor along said sloped portion of said support wall of said sensor retainer as said sensor is forced through said foil and out of said sensor retainer so that said sensor avoids said heat seal of said foil to said base portion.

* * * * *